(12) United States Patent
Sivo

(10) Patent No.: US 8,449,441 B2
(45) Date of Patent: May 28, 2013

(54) METHODS TO ARREST CANCER CELL GROWTH AND PROLIFERATION USING ELECTROMAGNETIC ENERGY DELIVERED VIA ELECTROMAGNETIC COIL SYSTEMS

(76) Inventor: Frank Sivo, Leonia, NJ (US)

( * ) Notice: Subject to any disclaimer, the term of this patent is extended or adjusted under 35 U.S.C. 154(b) by 1003 days.

(21) Appl. No.: 12/484,729

(22) Filed: Jun. 15, 2009

(65) Prior Publication Data

US 2010/0016651 A1 Jan. 21, 2010

Related U.S. Application Data

(60) Provisional application No. 61/129,749, filed on Jul. 16, 2008.

(51) Int. Cl.
*A61N 1/00* (2006.01)
(52) U.S. Cl.
USPC .......................................... 600/14
(58) Field of Classification Search
USPC ...................................... 600/9–15
See application file for complete search history.

(56) References Cited

U.S. PATENT DOCUMENTS

| | | | | |
|---|---|---|---|---|
| 4,674,481 | A * | 6/1987 | Boddie et al. .................... | 600/10 |
| 5,183,456 | A * | 2/1993 | Liboff et al. ...................... | 600/9 |
| 6,099,459 | A * | 8/2000 | Jacobson .......................... | 600/13 |
| 7,740,574 | B2 * | 6/2010 | Pilla et al. ........................ | 600/13 |
| 7,758,490 | B2 * | 7/2010 | Pilla et al. ........................ | 600/13 |

OTHER PUBLICATIONS

Ronchetto et al., "Extremely Low Frequency-Modulated Static Magnetic Fields to Treat Cancer: A Pilot Study on Patients With Advanced Neoplasm to Assess Safety and Acute Toxicity", Bioelectromagnetics, 25:563-571, 2004, 9 pages.
Barbault et al., "Amplitude-modulated electromagnetic fields for the treatment of cancer: Discovery of tumor-specific frequencies and assessment of a novel therapuetic approach", Journal of Experimental & Clinical Cancer Research, 28:51, Apr. 14, 2009, 10 pages.
Dandamudi et al., "External magnet improves antitumor effect of vinblastine and the suppression of metastasis", Japanese Cancer Association, 10.1111/j.1349-7006.2009.01201.x, Apr. 19, 2009, 7 pages.
Heller et al., "Electroporation for targeted gene transfer", Expert Opinion, 2(2), 2005, 14 pages.
Magnon et al., "Canstatin gene electrotransfer combined with radiotherapy: preclinical trials for cancer treatment", Gene Therapy, vol. 15, Jun. 12, 2008, 10 pages.
Hojman et al., "Physiological Effects of High- and Low-Voltage Pulse Combinations for Gene Electrotransfer in Muscle", Human Gene Therapy, vol. 19, Nov. 6, 2008, 13 pages.
Ivorra et al., "Use of conductive gels for electric field homogenization increases the antitumor efficacy of electroporation therapies", Physics in Medicine and Biology, vol. 53, Oct. 31, 2008, 14 pages.

(Continued)

*Primary Examiner* — John Lacyk
(74) *Attorney, Agent, or Firm* — Sheridan Ross P.C.

(57) ABSTRACT

A non-invasive method of using electromagnetic field energies to reduce or arrest the growth rate and proliferation of cancer cells, and induce apoptosis in cancer cells, relatively without significantly harming normal cells beyond their physiologic threshold of survival are provided. The methods described herein are intended to be used toward the treatment of cancer in human or animals within the context of cancer therapeutics.

22 Claims, 11 Drawing Sheets

OTHER PUBLICATIONS

Luukkonen et al., "Enhancement of chemically induced reactive oxygen species production and DNA damage in human SH-SY5Y neuroblastoma cells by 872 Mhz radiofrequency radiation", Mutation Research/Fundamental and Molecular Mechanisms of Mutagenesis, vol. 662, Dec. 24, 2008, 5 pages.

Yang et al., "The effect of high frequency steep pulsed electric fields on in vitro and in vivo antitumor efficiency of ovarian cancer cell line skov3 and potential use in electrochemotherapy", Journal of Experimental & Clinical Cancer Research, 28:53, Apr. 22, 2009, 9 pages.

Hou et al., "The in vivo performance of biomagnetic hydroxyapatite nanoparticles in cancer hyperthermia therapy", Biomaterials, Apr. 13, 2009, 5 pages.

Bruners et al., "Thermoablation of Malignant Kidney Tumors Using Magnetic Nanoparticles: An In Vivo Feasibility Study in a Rabbit Model", Laboratory Investigation, May 9, 2009, 8 pages.

Sisken et al., "Stimulation of rat sciatic nerve regeneration with pulsed electromagnetic fields", Brain Research, vol. 485, 1989, 8 pages.

Williams et al., "Therapeutic Electromagnetic Field Effects on Angiogenesis and Tumor Growth", Anticancer Research, vol. 21, 2001, 5 pages.

Rosenspire et al., Pulsed DC electric fields couple to natural NAD(P)H oscillations in HT-1080 fibrosarcoma cells, Journal of Cell Science, vol. 114 (8), 2001, 6 pages.

Rosenspire et al., "Real-Time Control of Neutrophil Metabolism by Very Weak Ultra-Low Frequency Pulsed Magnetic Fields", Biophysical Journal, vol. 88, May 2005, 14 pages.

Nelson et al., "Use of Physical Forces in Bone Healing", Journal of the American Academy of Orthopaedic Surgeons, vol. 11, No. 5, Sep./Oct. 2003, 17 pages.

Walker et al., "Electromagnetic Field Treatment of Nerve Crush Injury in a Rat Model: Effect of Signal Configuration on Functional Recovery", Bioelectromagnetics, 28:256-263, Jan. 30, 2007, 8 pages.

Heden et al., "Effects of Pulsed Electromagnetic Fields on Postoperative Pain: A Double-Blind Randomized Pilot Study in Breast Augmentation Patients", Aesthetic Plastic Surgery, 32:660-666, May 28, 2008, 7 pages.

Strauch et al., "Pulsed Magnetic Fields Accelerate Cutaneous Wound Healing in Rats", Journal of the American Society of Plastic Surgeons, Plastic and Reconstructive Surgery, vol. 120(2), Aug. 2007, 7 pages.

Pienkowski et al., "Comparison of Asymmetrical and Symmetrical Pulse Waveforms in Electromagnetic Stimulation", Journal of Orthopaedic Research, 10:247-255, 1992, 9 pages.

Reinbold et al., "Serum Plays a Critical Role in Modulating [Ca2+]c of Primary Culture Bone Cells Exposed to Weak Ion-Resonance Magnetic Fields", Bioelectromagnetics, 18:203-214, 1997, 12 pages.

Di Carlo et al., "Chronic Electromagnetic Field Exposure Decreases HSP70 Levels and Lowers Cytoprotection", Journal of Cellular Biochemistry, 84:447-454, 2001, 8 pages.

Di Carlo et al., "Mechanical and electromagnetic induction of protection against oxidative stress", Bioelectrochemistry, vol. 53, 2000, 9 pages.

Nuccitelli et al., "A new pulsed electric field therapy for melanoma disrupts the tumor's blood supply and causes complete remission without recurrence", Int. J. Cancer, vol. 125, Feb. 6, 2009, 8 pages.

Nuccitelli et al., "Nanosecond pulsed electric fields cause melanomas to self-destruct", Biochemical and Biophysical Research Communications, vol. 343, 2006, 10 pages.

Kirson et al., Alternating electric fields (TTFields) inhibit metastatic spread of solid tumors to the lungs, Clin Exp Metastasis, Apr. 23, 2009, 8 pages.

Kirson et al., "Alternating electric fields arrest cell proliferation in animal tumor models and human brain tumors", PNAS, vol. 104, No. 24, Jun. 12, 2007, 6 pages.

Kirson et al., Chemotherapeutic treatment efficacy and sensitivity are increased by adjuvant alternating electric fields (TTFields), BMC Medical Physics, 9:1, Jan. 8, 2009, 13 pages.

Zhang et al., "Effects of Different Extremely Low-Frequency Electromagnetic Fields on Osteoblasts", Electromagnetic Biology and Medicine, vol. 26, Jul. 1, 2007, 11 pages.

* cited by examiner (10MHz Carrier, Modulated at 200kHz, Duty Cycle = 40% (2uS "on" and 3uS"off"), normalized amplitude (10MHz Carrier, Modulated at 15 Hz, Duty Cycle = 0.0225% (1.5mS "on" and 65.1667mS "off"), normalized amplitude

METHODS TO ARREST CANCER CELL GROWTH AND PROLIFERATION USING ELECTROMAGNETIC ENERGY DELIVERED VIA ELECTROMAGNETIC COIL SYSTEMS

CROSS REFERENCE TO RELATED APPLICATIONS

This application claims the benefit of U.S. Provisional Application No. 61/129,749, filed Jul. 16, 2008, the entire disclosure of which is hereby incorporated herein by reference.

FIELD OF INVENTION

The present invention is generally related to cancer treatments using electromagnetic energy.

BACKGROUND

Electric fields of endogenous origin have been measured outside the periphery of cultured cells, within multiple tissues and cell types of developing embryos, and at the borders of healing and regenerating tissues. Electrically charged and charge-dependent molecules of cells and tissues are naturally inherent to biologic systems and assist in defining their electro-physiologic and functional properties, thereby permitting them to self-regulate and interact with their associated molecules and related biologic systems. At the molecular level of all cells, tissues and organs, the physiologic and biochemical processes directing cell survival, growth, proliferation, function such as programmed cell death require a complex series of fundamental alterations and modifications in the electrostatic bonding interactions within their given bio-regulatory systems. These charge-dependent cell governing bio-regulatory systems are in fact naturally inherent within all living cells and tissues. Certain exogenously applied electromagnetic fields of low energy have been demonstrated to alter cell membrane signaling systems, cell membrane potentials, oxidative/reductive processes and rates, DNA transcription, thermodynamic and kinetic driven protein folding, ion drift and collision rates, immune cell response, and enzyme activity when applied to biologic systems.

Making use of this phenomena, electromagnetic fields of low energy have been used therapeutically for several years or more to stimulate bone growth and repair, as well as healing of other various tissues in humans and animals.

SUMMARY

In the context of cancer therapeutics, there are physiologic differences between normal cells and cancer cells which render the cancer cells with different sensitivity than normal healthy cells to the electromagnetic field applications described herein. The methods and applications described for electromagnetic field inductive coupling to cancer cells and cancerous tumor tissues are utilized to adversely affect the cancer cell's bio-regulatory growth, proliferation and survival systems without harming, beyond a physiologic lethal tolerance, the bio-regulatory growth, proliferation and survival systems of surrounding non-pathologic normal cells and tissues. That is to say, embodiments of the present invention are directed specifically toward adversely altering the bio-regulatory electrical energies of cancer cells, specifically, the bio-regulatory electrical energies that are involved in the physiologic processes of cancer cell growth, proliferation, and survival.

Embodiments of the present invention accomplish this without lethally affecting the bio-regulatory systems of normal cells and tissues.

Methods are provided for introducing exogenously applied electromagnetic field energy of specific signal parameters into a biological system of cancer cells and cancerous tumor tissues. This provides the ability to induce growth arrest and apoptotic cell death in cancer cells and cancerous tumors via the electromagnetic field's energy affect upon the bio-regulatory electric energies of that cancerous system.

Specifically, in the context of the cancer therapeutic process, methods for electromagnetic field inductive coupling to biologic tissues are utilized for the purpose of adversely affecting, beyond a tolerance of normal biologic homeostasis, the bio-regulatory electric energy interactions that govern the biologic, biochemical, biophysical and physiologic processes of cancer cells and cancerous tumor growth and proliferation. Cancer cell growth arrest and apoptosis are the results demonstrated via applying to cancer cells and cancerous tumor tissue the electromagnetic field energies that are a function of the electromagnetic signal parameters described in this invention.

Embodiments of the present invention are based on investigations which demonstrate an increase in cancer cell and cancerous tumor programmed cell death (apoptosis) as well as an adverse affect on the cancer cells growth and proliferation cycles. These findings are the results of inductive coupling of electromagnetic field energies of specific frequencies, waveforms and intensities to cancer cells grown in an in vitro setting, as well as cancerous tumor tissues residing in living mice during in vivo experimental study model trials.

Embodiments of the present invention are intended for use as a means to induce growth arrest and/or apoptosis in cancer cells and cancerous tumors via the externally applied application of electromagnetic field energies of specific frequency range, waveform and intensity range to the cancer cells and cancerous tumors. An electromagnetic transducer(s) e.g. coil(s) of any design or configuration that is (are) capable of producing said electromagnetic field energy may be employed as the tool for delivery of the electromagnetic field energy to the cancer site of interest. Any of a variety of electrical signal generators can be used to provide alternating (e.g., sinusoidal, square, sawtooth, etc.) current that can be amplified to the desired radio-frequency power levels and modulated to give the desired signal characteristics such as envelope shapes and repetition rates. This signal is used to drive electromagnetic coils with a current that will generate a time varying magnetic field, B. The magnetic field penetrates the biologic tissue and induces an electric field in the tissue.

To optimize the transfer of power from the signal generator and the amplifier into the tissue, a tuner or alike may be used to match the electrical impedances. The electromagnetic field energy is delivered to the cancer site of a patient by anatomically positioning an electromagnetic coil or multiple coil assembly on, around, or about the outer skin surface of the patient. The electromagnetic coil assembly is positioned to deliver the highest quality, in terms of bio-effectiveness, electromagnetic field energy possible to the area of the cancer and or tumor site to be treated.

One aspect of the present invention is to provide a particularly configured electromagnetic field to a cancer site where the electromagnetic field either has or is generated by electrical current having a particular waveform, frequency range and field intensity range. Moreover, embodiments of the present invention utilize electromagnetic field signal parameters which include the harmonics and infinite sub-harmonics of any one or more of the particular signal parameters provided herein, particularly when such parameters have demonstrated cell growth arrest and apoptosis in cancer cells and live cancerous tumors specifically.

One aspect of the present invention is to provide an electromagnetic field energy delivery to a patient via non-invasive electromagnetic field producing instruments that are capable, by way of inductive coupling, to deliver the electromagnetic field energies to the targeted cancer cells and tumor tissues of interest. The electromagnetic field signal parameters described herein are intended to be used specifically as a tool to induce cancer cell growth arrest and apoptosis specifically in the context of cancer therapeutic treatment.

In accordance with at least some embodiments of the present invention, non-invasive methods for the delivery of the electromagnetic field energy to the area of cancer growth in the patient are used. That is to say, the electromagnetic field energy parameters can be delivered via any externally placed electronic device that can serve the purpose of delivering the designated signal by means of electromagnetic field energy to the patient during treatment and attain the desired biologic effect.

In accordance with at least some embodiments the mode of energy transfer between the electronic device and the patient is electromagnetic field/tissue inductive coupling of energy.

It is also one aspect of the present invention to employ electromagnetic transducer(s) such as a coil(s) type of devices for the purpose of delivering electromagnetic field energy via a method of electromagnetic field/tissue inductive coupling to a patient, due to the fact that the electromagnetic field signal parameters used herein are specifically designated to cause growth arrest of cancer cells and death of cancer cells via apoptotic pathways specifically, and not to stimulate or promote tissue growth, or enhance the healing and regeneration of damaged tissues.

As can be appreciated by one skilled in the art, the electromagnetic field signal parameter ranges discussed herein are intended for delivery to a patient via any of the various possible designs of exterior body-positioned electromagnetic transducers, e.g. coils, electromagnetic field producing instruments or device systems, capable of delivering said electromagnetic field energies and attaining the desired biologic effect.

The biological effect to the cancer cells or cancerous tumors resulting from application of the electromagnetic energy signal parameters herein are not a result of excessive levels of heat, radiation, electric current, or high electric voltage that would typically be considered lethal and destructive to both, cancer cells and cancerous tumors as well as normal cells and normal tissues. The electromagnetic energy levels described herein cause adverse growth effects and cell death to cancer cells and cancerous tissues, without causing lethal damage and destruction to normal cells and tissues.

Other past solutions that use similar electromagnetic field signal parameters for the treatment of cancer describe the use of surgically invasive inserted electrodes made of wire or other materials capable of electric conduction.

DETAILED DESCRIPTION

Embodiments of the present invention provide an electrotherapeutic system of employing electromagnetic field energies to a human or animal for the purpose of inducing growth arrest and cell death in cancer cells and cancerous tumors that reside in the body of animals or humans. The electromagnetic fields can be synthesized by any type of the many varieties of signal generators, signal amplifiers, and geometrically configured electromagnetic coil designs. For example, with reference to FIGS. 1-3, these diagrams represent three different types of electromagnetic coil configurations that can be selected and used to apply the signal by means of electromagnetic field for treating cancer.

Figure 1:
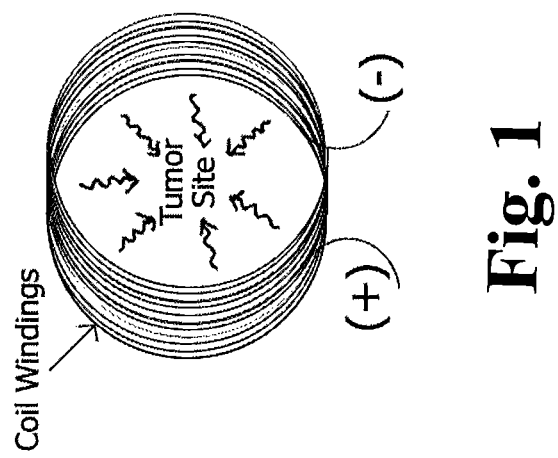
FIG. 1 is a schematic representation of a first exemplary transducer placed in a position to treat a tumor site.

The exemplary embodiment depicted in FIG. 1 represents the solenoid design type that utilizes wire windings of various circular dimensions to carry electric current and induce electromagnetic fields. The induced electric fields are strongest at the wires and inside the perimeters of the coil boundaries where the targeted cancer tissue can be located during patient treatment.

Figure 2:
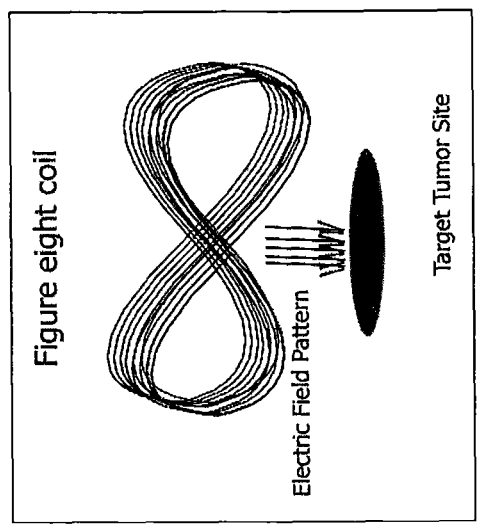
FIG. 2 is a schematic representation of a second exemplary transducer (figure eight coil winding) placed in a position to treat a tumor site.

FIG. 2 depicts another exemplary embodiment where a figure eight design type is used whereas the wire windings are configured in the shape of the number eight and these wire windings carry electrical current used to induce electromagnetic fields. The induced electric fields are typically the strongest perpendicular to the center area of the figure eight coil at a point where the windings cross one another and thus it is this area that would be most effective during treatment of a cancerous tumor in a patient.

Figure 3:
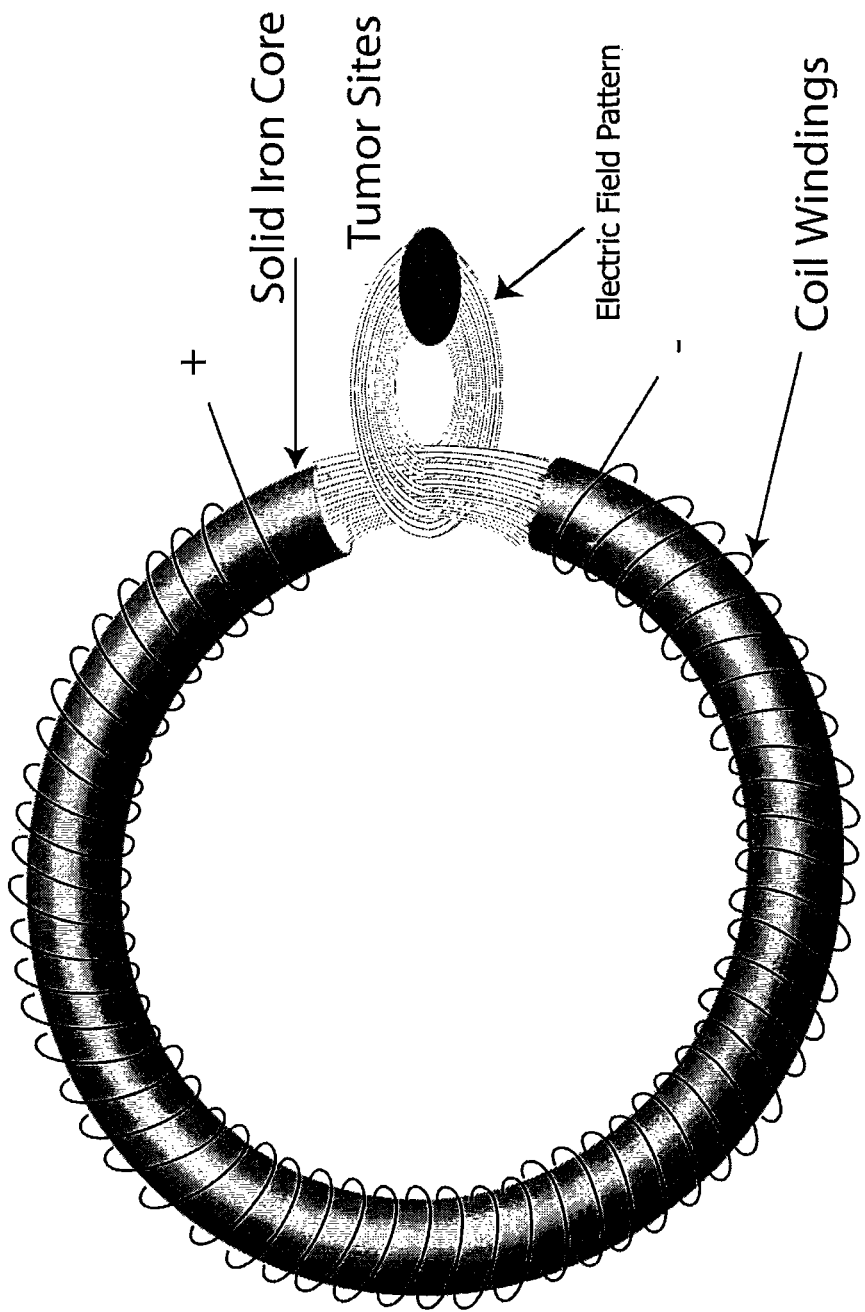
FIG. 3 is a more detailed depiction of a exemplary transducer and its interaction with a tumor site.

FIG. 3 depicts another exemplary embodiment where a solid ferrite core type design is used and is electrically energized via wire wrappings around a solid iron or ferrite core. The current induces a magnetic field in the iron core and the magnetic field is transmitted across the open gap. The induced electric field is substantially oriented at a right angle to the magnetic field and the targeted cancer cells and cancerous tumor tissues are placed such that they are exposed to these fields. The coil depicted in FIG. 3 may be placed such that the targeted area of interest on the patient would fall adjacent to the gap in the iron core.

Figure 4:
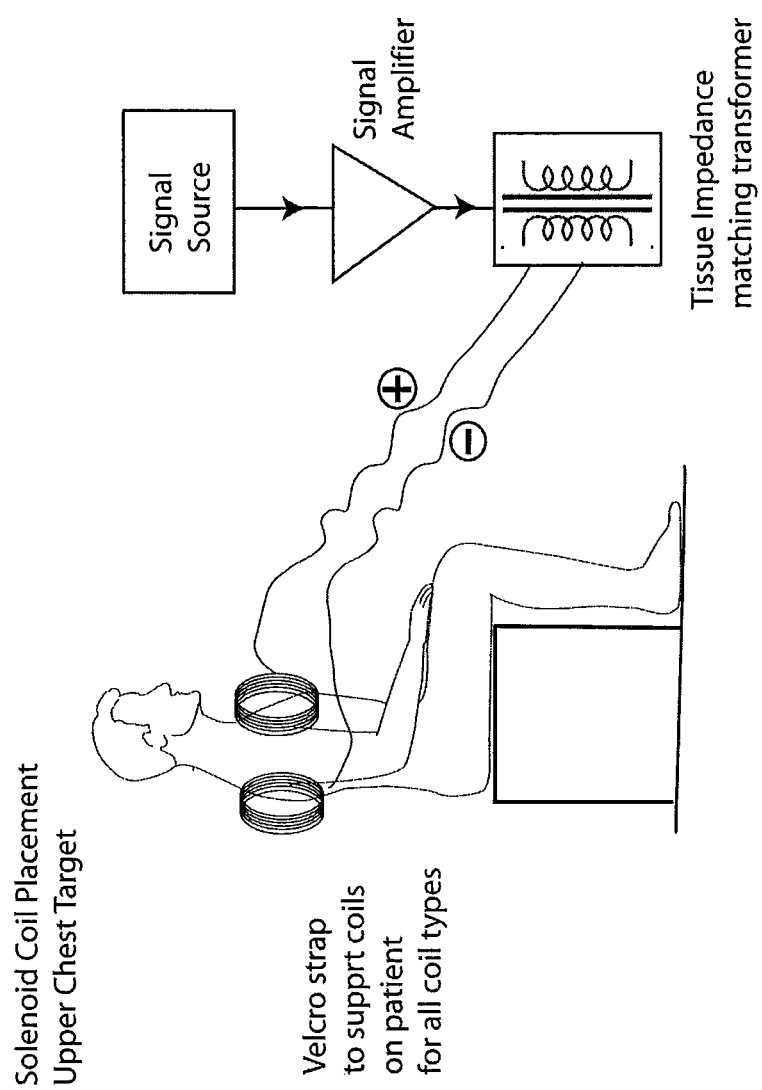
FIG. 4 is a block diagram depicting a first exemplary cancer treatment system.
Figure 5:
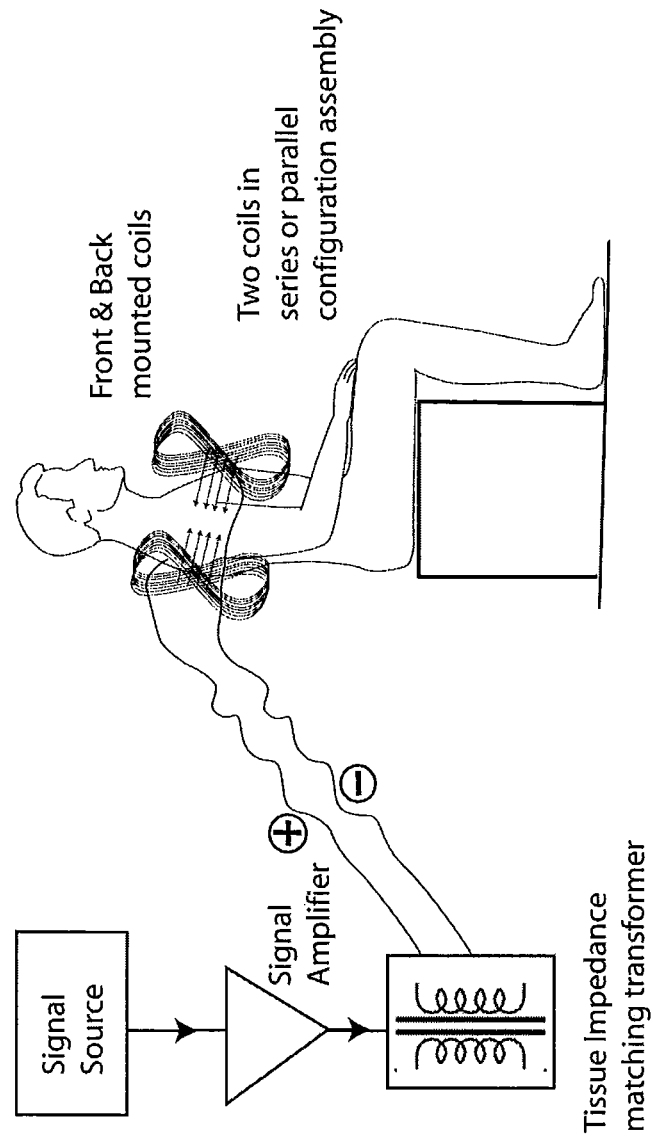
FIG. 5 is a block diagram depicting a second exemplary cancer treatment system.
Figure 6:
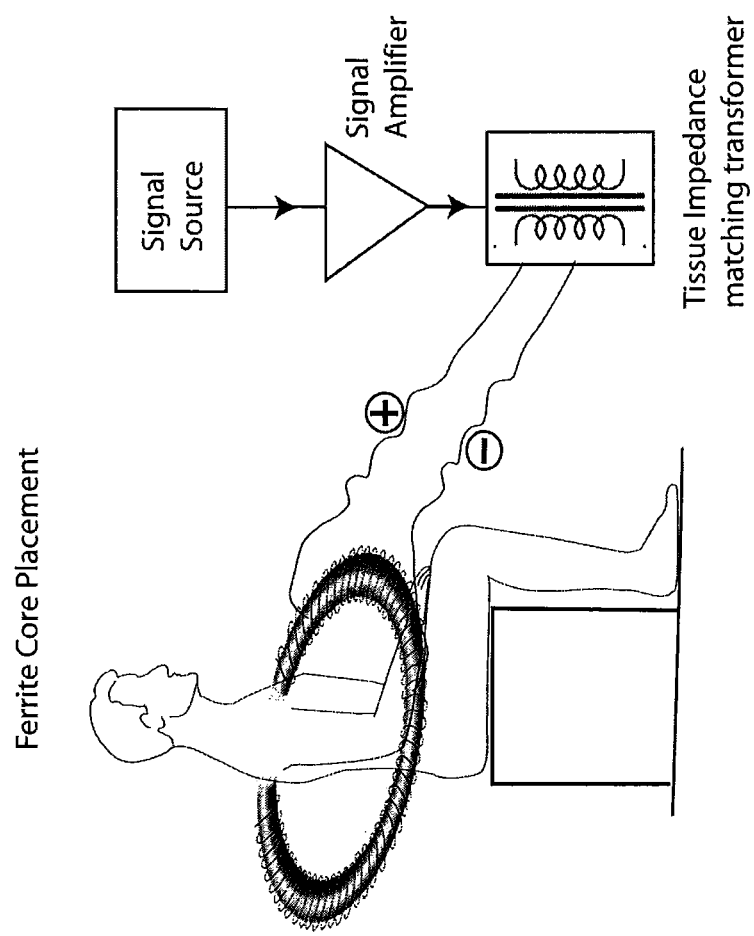
FIG. 6 is a block diagram depicting a third exemplary cancer treatment system.
Figure 7:
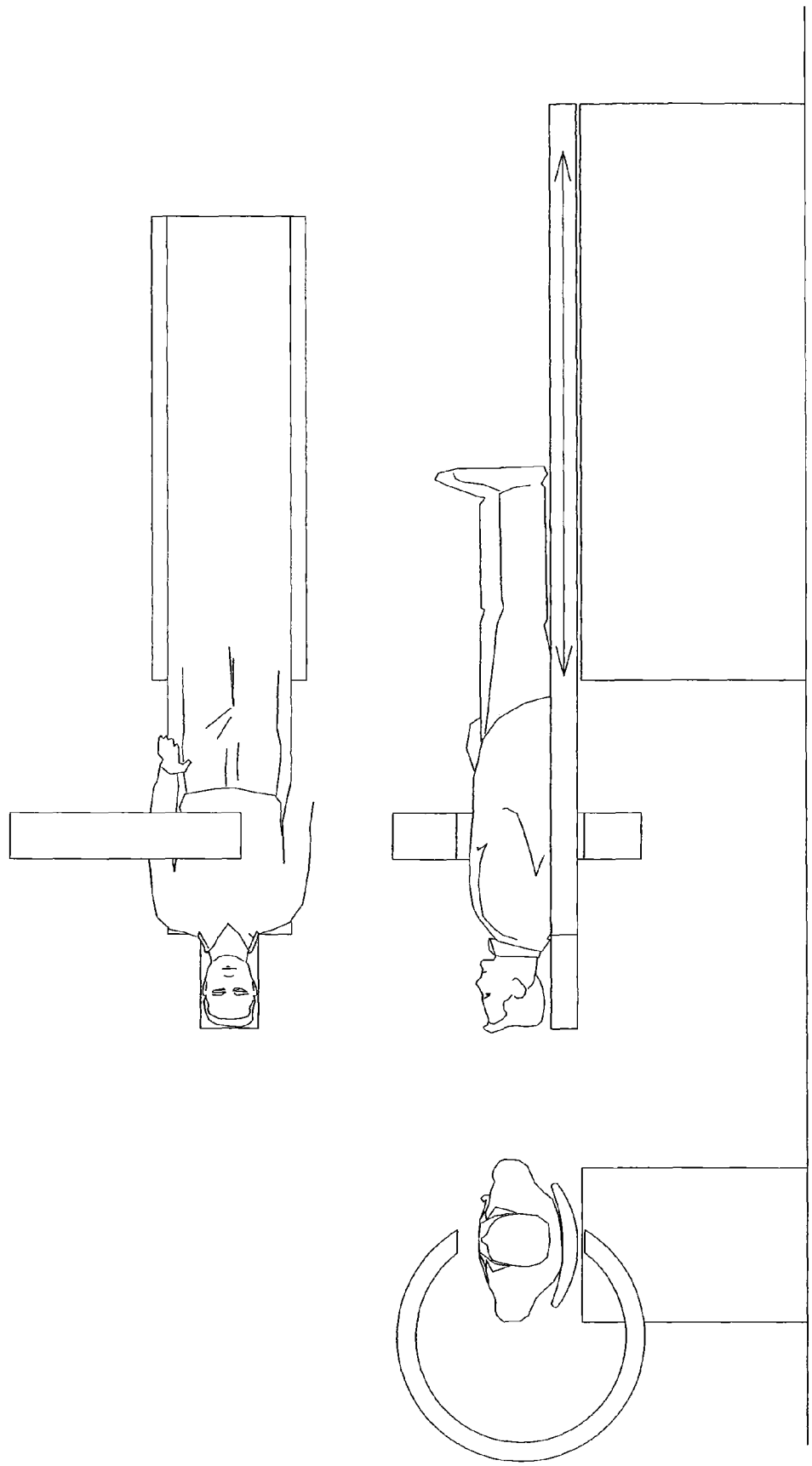
FIG. 7 is a block diagram depicting a fourth exemplary cancer treatment system.
Figure 8:
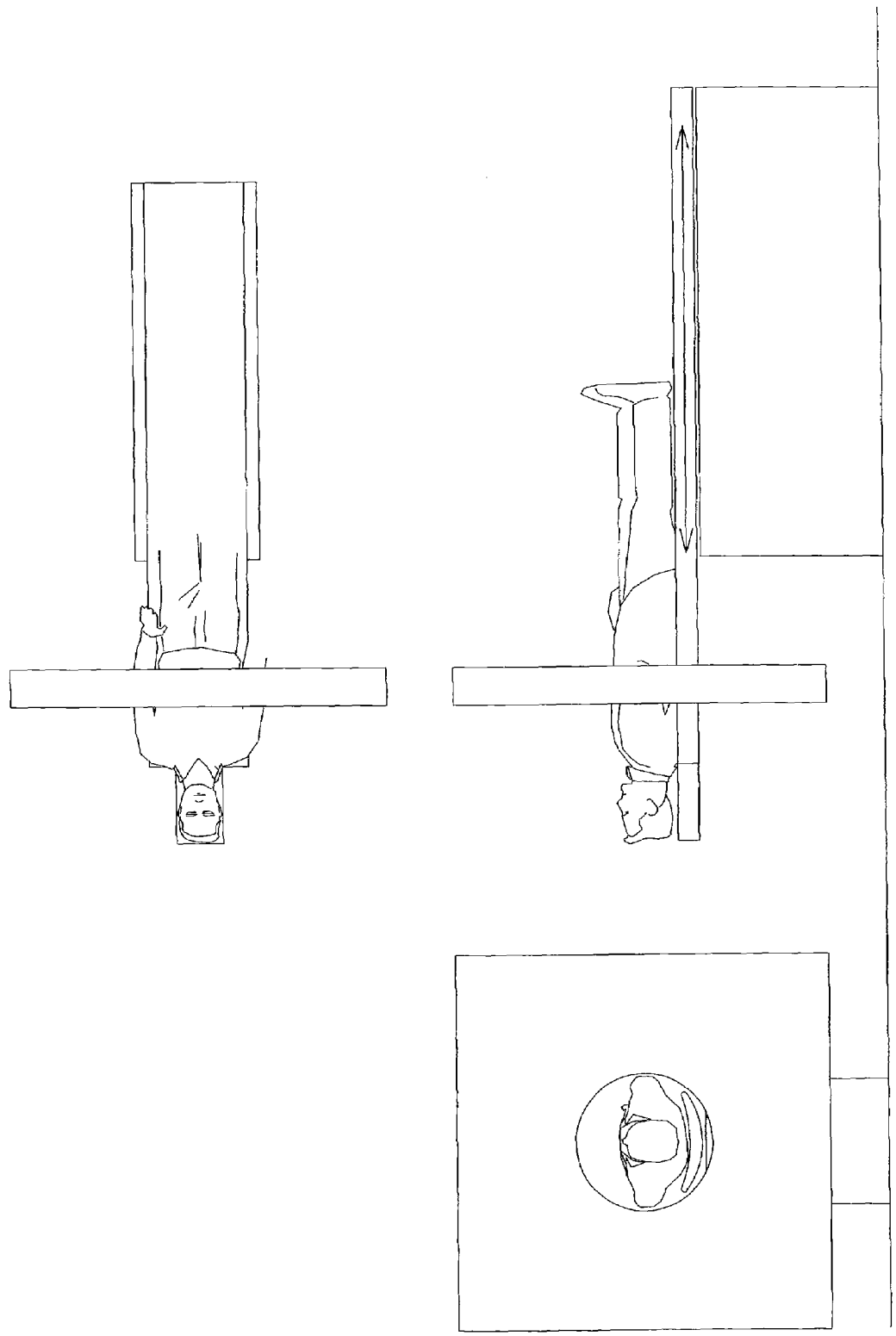
FIG. 8 is a block diagram depicting a fifth exemplary cancer treatment system.
Figure 9:
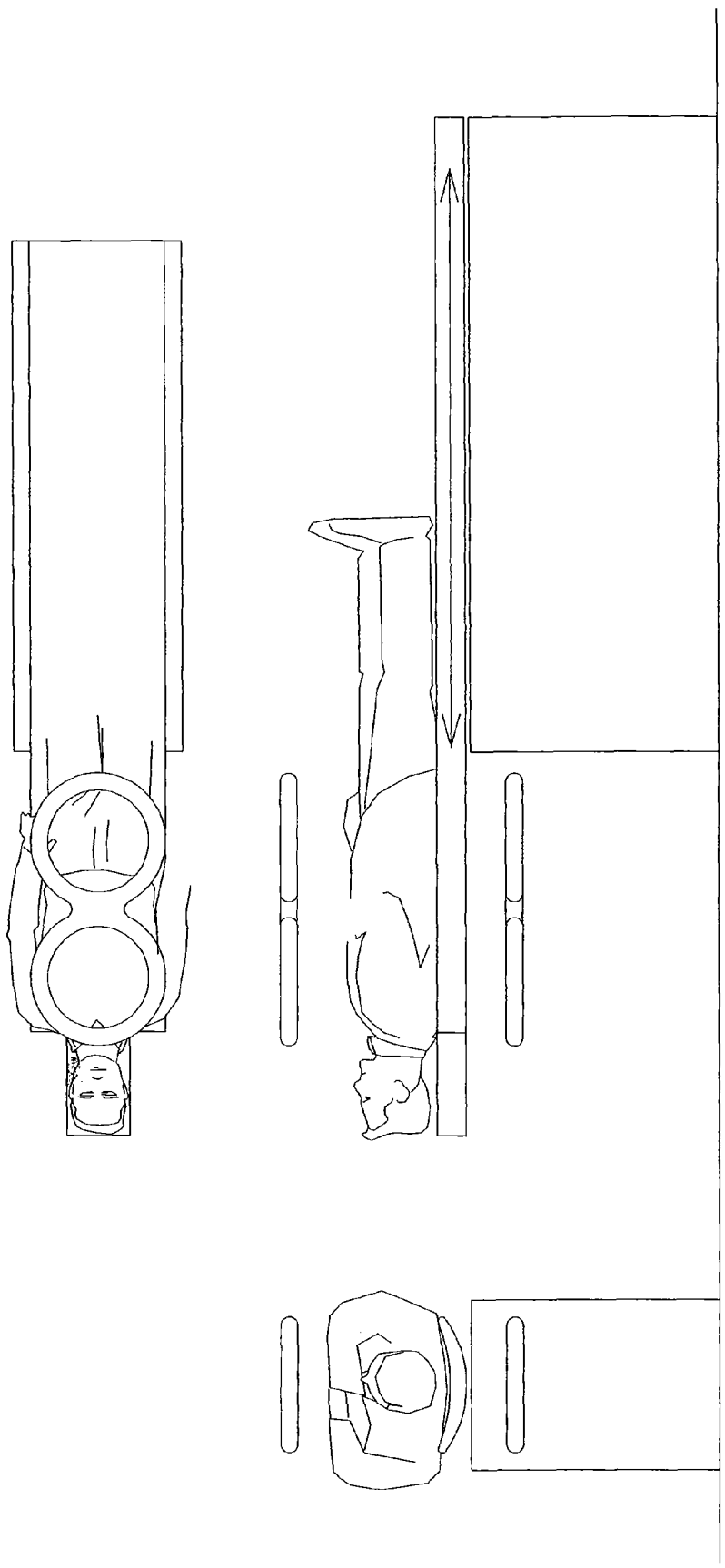
FIG. 9 is a block diagram depicting a sixth exemplary cancer treatment system.

FIGS. 4-6 depict examples of various types of portable coil apparatuses and systems that can be used during treatment application for the delivery of an electromagnetic field to the patient. In accordance with at least some embodiments of the present invention, the coil apparatuses may be secured to the patient via a non-conductive means, such as by using fabric or other non-conductive materials. Alternatively, or in addition, the coils may be placed on the patient and held in place by gravity. As another alternative, the coils may be secured to the patient with a preconfigured device that is capable of conducting electricity and generating its own electromagnetic field, which can be used to supplement or direct the electromagnetic field generated by the primary coil apparatus.

Figure 10:
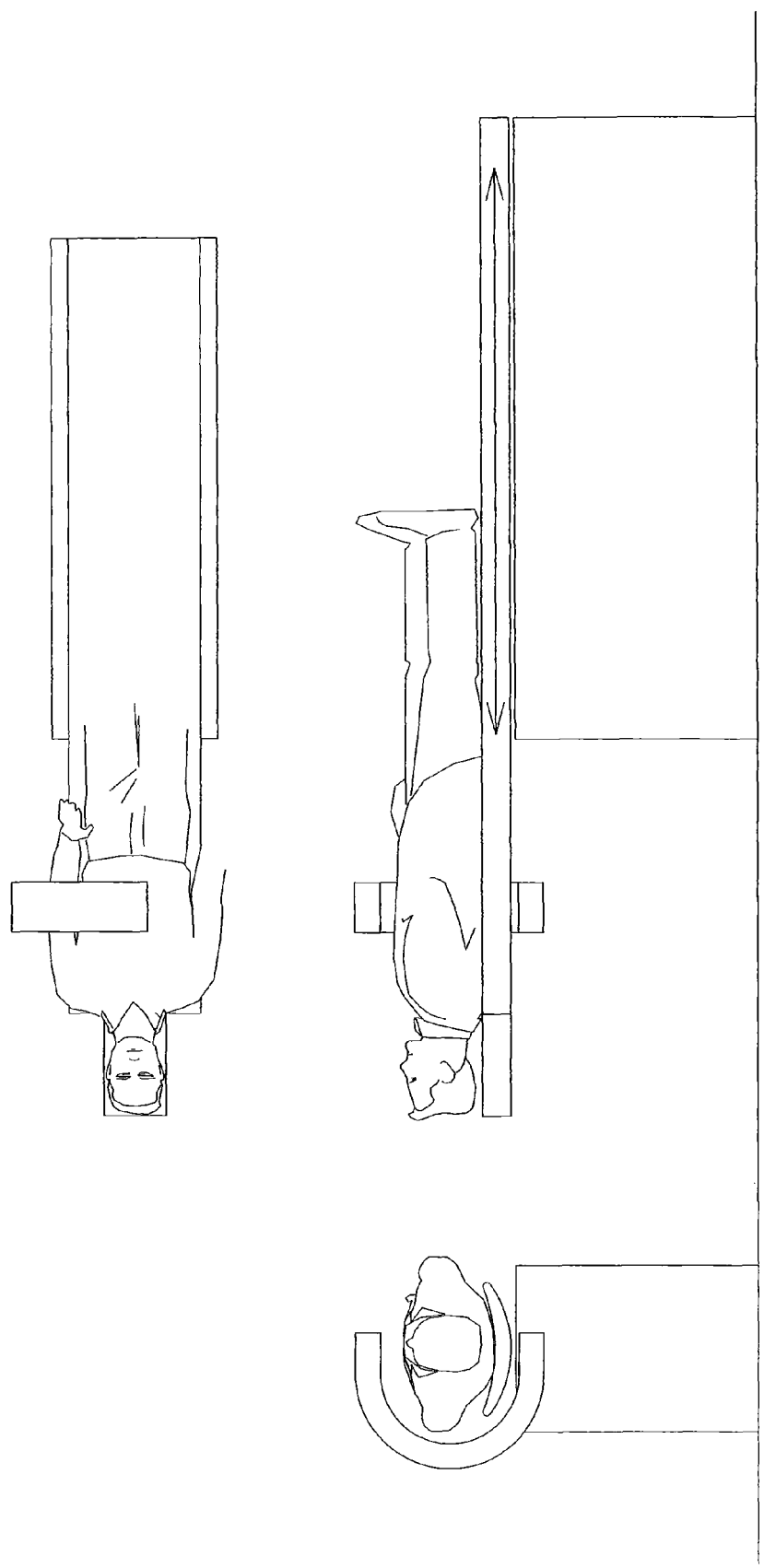
FIG. 10 is a block diagram depicting a seventh exemplary cancer treatment system.

As an alternative to using portable coils, or in addition to using such coils, embodiments of the present invention also contemplate the use of a stationary coil or set of coils that can be configured to have a patient moved into and about such coils. Such exemplary embodiments are depicted in FIGS. 7-10 where it is shown that the stationary table design types of coil assemblies can be used for application of electromagnetic energy to a patient in the clinical setting, where the patient is resting on the table during the electromagnetic field delivery. More particularly, embodiments of the present invention may be adapted to employ a clam-shell coil configuration (FIG. 7), a full coil configuration (FIG. 8), one or two opposing figure eight coils (FIG. 9), and/or a c-shaped coil (FIG. 10). One or more of such exemplary electromagnetic energy delivery systems may be described in further detail in one or more of the following patent documents, each of which are hereby incorporated herein in their entirety: U.S. Pat. No. 7,160,241; U.S. Pat. No. 6,060,293; U.S. Pat. No. 5,723,001; U.S. Pat. No. 4,998,532; U.S. Pat. No. 4,454,882; U.S. Pat. No. 5,014,699; U.S. Pat. No. 4,674,482; U.S. Pat. No. 6,208,892; U.S. Pat. No. 6,856,839; US 2001/0021868.

The electromagnetic energy field generated by a coil and applied to a patient in accordance with at least some embodiments of the present invention is composed of current and voltage (i.e., is generated in a coil or similar conductor at a particular voltage and current level) to induce a particular magnetic field. The electromagnetic field may be synthesized by one or multiple electrically energized electromagnetic coils that are connected via terminals and cables to an electric signal source. That is to say, a single coil or multiple coils are driven by a signal source from a suitable or commercially available signal generator with an output current that is amplified by a suitable or commercially available amplifier. The amplified signal is then delivered to a coil which can be made of various electric conducting materials (e.g., steel, copper, aluminum, gold, silver, etc.), and that may be configured the same, similar, or different from the coils referred to FIGS. 1-3, and whereby the current traveling through the coil material produces a magnetic field.

The magnetic field is adapted to induce an electric field, thus the electromagnetic field is produced. During treatment applications on a patient, and with a coil assembly as described above positioned on, about, or around the tissue area of choice, the electromagnetic field then inductively couples to the dielectric pathways of the targeted cell or tissue of interest, thereby inducing electrical potential in the targeted cell or tissue, and inducing the desired biophysical event. To optimize the uniformity of the electromagnetic field lines and induced voltage in the targeted tumor tissues, it is recommended that the size of the coil that is used for treatment of the tumor be determined with consideration to the anatomical location and size of the tumor area being treated. Situations can arise where impedance miss-match between the coil and tissues can occur as a result of coil placement on, about or around the body. The coil/tissue inductive coupling event can be optimized to deliver the most appropriate and required electromagnetic energy via a process of impedance-matching. Impedance-matching is made possible with the use of an impedance-matching transformer that is typically located between the output of the amplifier and input of the coil structure.

One of the embodiments of this invention includes a signal comprised of modulated-bursts of a sine wave (or similar type of wave), and this electromagnetic energy is delivered to the area of cancer growth at a pre-determined amplitude range. The amplitude of the electromagnetic wave is set by controlling the current output from the current source to the amplifier. The electromagnetic signal parameters found to be effective in reducing cancer cell proliferation and inducing cancer cell apoptosis are within a particular range. However, the biology of cancer is such that cancer cells and cancerous tumors demonstrate a wide heterogeneous biologic nature, and it is recognized scientifically that widespread histological diversities exist among the various anatomical regions in the body where cancer may be located. Therefore, the electromagnetic field signal parameters that can be altered to optimally treat a cancerous cell but not harm a normal cell include, but are not limited to, waveform, peak field strength, carrier frequency, duty cycle, burst duration time, rise and/or fall times, and burst repetition rate. The particular combination of values for each parameter may vary across a certain range depending upon certain mentioned biologic factors. These biologic factors include, but are not limited to, specific cancer cell genotype, phenotype, cell sensitivity, and variables within the biologic, physiologic, biophysical and biochemical properties of the specific cancer cells or cancerous tissues being treated. The absorption of the signal by the biologic material occurs over a range of frequencies so that it is expected there will be a range for frequencies corresponding to the line width of the absorption spectra of the biologic processes being excited or activated by the applied signal. Accordingly, the impedance matching transformer may be employed and may have as an input to its control mechanism one or more sensors connected to the patient that are adapted to measure one or more of the biologic factors of interest.

The variation of electromagnetic field signal properties within the electromagnetic field signal parameter range that are necessary to address the above biologic factors includes, but is not limited to, waveform type, carrier frequency, burst duration and width, duty cycle, burst repetition rate, rise and/or fall time, and peak amplitude. These electromagnetic field signal parameters are expected to range over the bandwidth of the response time for the biologic tissue being addressed. This can be done in order to demonstrate effectiveness in terms of cancer cell growth arrest and the induction of cancer cell and tumor apoptosis. The electromagnetic field signal parameters found to be effective for cancer cell growth arrest and apoptosis induction are multiple signal components to include any Fourier components within the spectral parameters of the pulsed-modulated bursts of sinusoidal bipolar radio-frequencies described in this invention.

As can be appreciated by one skilled in the art, electromagnetic field signal parameters used can be inclusive within the parameters or range of parameters discussed herein for use relative to the treatment of cancer and cancerous tumors in animals or humans.

Figure 11:
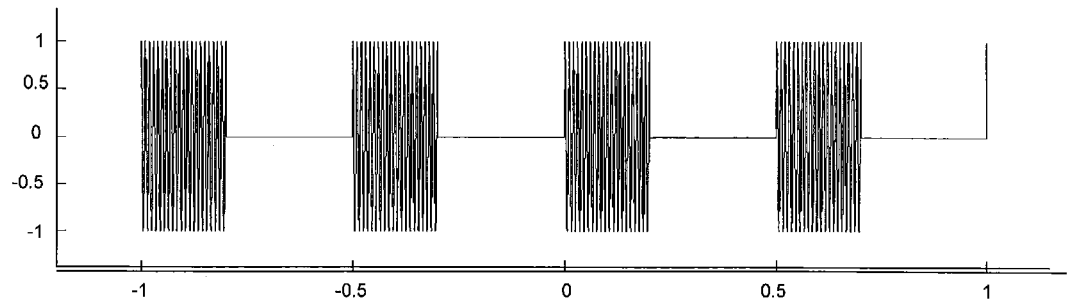
FIG. 11 depicts an exemplary waveform used for treating cancer in accordance with at least some embodiments of the present invention.

As one example, and as can be seen in FIG. 11, about a 100 kHz to about 1 GHz bipolar sinusoidal waveform, or preferably a 1 MHz to 100 MHz bipolar sinusoidal waveform, or more preferably about a 10 MHz bipolar sinusoidal waveform (where the frequency of the waveform is maintained low enough to avoid tissue heating), when properly gaited using a signal control unit, and when delivered to the tissue site of interest as a pulse modulated burst width of between about 0.2 microseconds and about 20 microseconds, or preferably between about 1 microsecond and about 10 microseconds, or more preferably about 2 microseconds duration, (20 cycles/burst) and at a burst repetition rate of between about 100 and 300 kHz, or preferably between about 150 kHz and 250 kHz, or more preferably about 200 kHz has demonstrated successful biological effectiveness in the context of arresting cancer cell growth and proliferation, and inducing cancer cell apoptosis in cancerous tumors of living mice. This particular waveform may be applied with any of the coil devices or system described herein. For instance, any suitable portable or stationary electromagnetic coil device or electric field producing device thereof, capable of delivering the electromagnetic energy signal to the cancerous tumor site, and within the guidelines, parameters, and specifications as described in this invention, can be employed.

Figure 12:
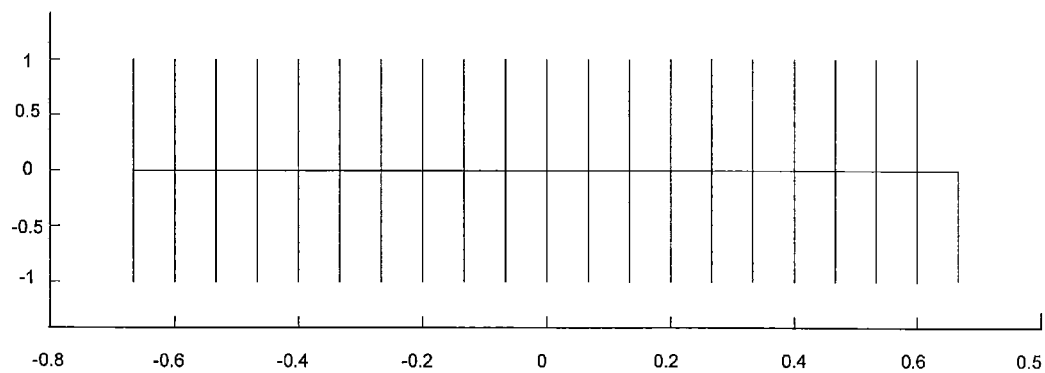
FIG. 12 depicts an exemplary waveform used for treating cancer in accordance with at least some embodiments of the present invention.

As another example, and as can be seen in FIG. 12, about a 100 kHz to about 1 GHz bipolar sinusoidal waveform, or preferably a 1 MHz to 100 MHz bipolar sinusoidal waveform, or more preferably about a 10 MHz bipolar sinusoidal waveform that is properly gaited by using a signal control unit, and when delivered to the tissue site of interest as a pulse modulated burst width of between about 0.015 milliseconds and about 150 milliseconds, or preferably between about 0.15 milliseconds and about 15 milliseconds, or more preferably about 1.5 milliseconds duration, (15,000 cycles/burst), and a burst repetition rate of between about 0.15 Hz and about 1.5 kHz, or preferably between about 1.5 Hz and about 150 Hz, or more preferably about 15 Hz has demonstrated successful biologic effectiveness in the context of cancer cell growth arrest and apoptosis induction in cancerous tumors of living mice. This particular waveform may be applied with any of the coil devices or system described herein. For instance, any suitable portable or stationary electromagnetic coil device or electric field producing device thereof, capable of delivering the electromagnetic energy signal to the cancerous tumor site, and within the guidelines, parameters, and specifications as described in this invention, can be employed.

The solid ferrite type of coil may be used to optimize certain frequencies used in this invention, thereby helping to reduce the power required to drive this coil. The electromagnetic field peak amplitude levels for both of the pulse-modulated radio-frequency burst signals described above that demonstrate decreased cancer cell growth, proliferation, and apoptosis, when applied to cancer cells or tumors during the time points and vulnerable cell cycle periods as described below, are in a range of about 1 to 300 V/cm, or peak amplitudes that are less than that which causes significant or sustained damage to (most) normal cells or tissues. More specifically, embodiments of the present invention contemplate that some damage may occur to some normal cells around a targeted region of cancer cells, but such damage should be limited in terms of the size and scope (e.g., if a tumor is being treated in a liver or similar internal organ, then some healthy tissues in the internal organ and surrounding areas may be damaged, but the extent of such damage should be limited by properly controlling the characteristics of the electromagnetic field). The current density of these fields would be in the range of several amps per meter squared, and this value is dependent on the tissue impedance being targeted and exposed during patient treatment.

In the context of the cancerous tumor environment, the growth and division regulatory cell cycles of cancerous tumor cells typically are not collectively synchronized with one another. In terms of cell sensitivity to the electromagnetic field energies, many of the diverse cancer cell genotypes and or phenotypes that make up the tumor proper have individual critical points in their growth and division cell cycles as a function of biological timing and molecular vulnerability. It is therefore clarified that in order to attain success in arresting cancer cell growth and/or inducing cancer cell or cancerous tumor cell apoptosis, the electromagnetic field energies described herein and used in accordance with at least some embodiments of the present invention should be presented and/or delivered to any tumor cell of therapeutic treatment interest during at least one or more critical cell cycle biological time points or molecular vulnerability points or relevantly sensitive points within that given tumor cell.

The final effect from the electromagnetic field energies delivered to the area of cancer is inhibition of the cancer cells growth cycle, decreased cancer cell growth rate, and cancer cell apoptosis. It has been determined that the outcomes of applying electromagnetic field signals to cancer growth in tumors residing in living mice that the above electromagnetic signal parameters are effective in arresting cancer cell growth and inducing cancer cell apoptosis.

EXAMPLES

To insure adequate tumor development the immuno-compromised mouse strain ICR-scid was chosen for these experiments. Four male mice were injected with a human pancreatic cancer cell line for the purpose of inducing tumor development. Ample time was allowed for tumor development in each mouse. Two mice were used for electromagnetic field exposure application and two were used as a non-exposed control group.

Three different coil configurations as shown in FIGS. 1-3 were individually tested as part of this study. Individual coils were applied directly over the tumor site of the mouse in a manner that allowed for inductive coupling of the electromagnetic field signal into the area of the mouse tumor. The two mice were exposed individually throughout all periods of the tumor growth cycle. The electromagnetic signal parameters described in the detail section of this invention were applied for each individual mouse that was exposed. The tumors of all four mice were surgically removed five days after the finish of the last exposure application and preserved in formalin. Each individual tumor was then sectioned into three individual areas and the tumor tissues processed and mounted on glass slides for histo-chemical study. The tissues of the tumor samples were stained using TUNEL staining which is one of the current standards for detection of apoptosis. The slides were read using fluorescence microscopy and six photographs of each tissue section were acquired. The TUNEL staining was quantified in the following manner. All images were acquired with the same exposure and gain settings. For each field, the total TUNEL fluorescence per nucleus was quantified. Nuclei were defined by thresholding the DAPI signal. The threshold image was used as a mask on the TUNEL image to define nuclear TUNEL labeling. The masked TUNEL image was thresholded and the integrated intensity was calculated. Nuclei were counted manually in each field using DAPI labeling. Total apoptotic activity was calculated as nuclear TUNEL integrated intensity.

Experiment results demonstrate a substantial increase of up to and above 50% in the level of apoptotic related cell death in the electromagnetic field exposed mouse group when compared to the unexposed mouse control group when using certain exposure parameters, numerical differences in terms of the level of cell apoptotic activity vary between the two exposed mice on an individual basis, and there is a numerical variation of cell apoptosis measured among individual tissue sections corresponding to anatomical depth within the same tumor. This most likely reflects electromagnetic field differences in terms of field amplitude relative to distance from various sections of the tumor. This experiment was repeated with similar results.

While embodiments of the present invention have been described in connection with particular apparatuses, methods, systems, and system components, the invention is not so limited. Moreover, one skilled in the art will appreciate that each feature of the present invention described herein may be separately claimable. Furthermore, embodiments of the present invention are not necessarily limited to the treatment of cancerous cells, although experimental data has been produced showing positive results when used on such cells. Rather, embodiments of the present invention may also be used to target any particular type of cell (whether cancerous or not) based on its characteristics and to impart a particular reaction from that cell or group of cells having the common characteristic. The reaction imparted may be controlled by intelligently adjusting the parameters of the electromagnetic field applied thereto.

What is claimed is:

1. An apparatus, comprising:
a transducer adapted to conduct current;
a current generator adapted to induce a current flow in the transducer; and
wherein the transducer is located proximate to a tumor site and a healthy cell site such that when current flow is induced in the transducer an electromagnetic field is produced that induce cancer cell growth arrest and/or apoptosis in the tumor site by generating an electromagnetic field that comprises a peak amplitude greater than 100 V/cm.

2. The apparatus of claim 1, wherein the transducer comprises a coil winding and wherein the current generator generates at least a 10 MHz bipolar sinusoidal current.

3. The apparatus of claim 2, wherein the current is pulsed for a predetermined duration at a predetermined pulse rate.

4. The apparatus of claim 3, wherein the predetermined pulse duration is between about 1 and 2 microseconds in duration.

5. The apparatus of claim 3, wherein the predetermined pulse duration is less than or equal to about 1.5 milliseconds in duration.

6. The apparatus of claim 2, wherein the current is modulated at less than about 20 Hz.

7. The apparatus of claim 2, wherein the current is modulated at about 15 Hz.

8. The apparatus of claim 2, wherein the current comprises at least one of a sine, square, triangle, sawtooth, and rectangular waveform.

9. The apparatus of claim 1, further comprising an impedance matching transformer residing between the current generator and the coil winding, wherein the impedance matching transformer is adapted to adjust the current provided to the coil winding so as to maximize the coupling of the electric signal into the biologic tissue.

10. The apparatus of claim 1, wherein the electromagnetic signal comprises an original signal, including Fourier components of the original signal.

11. The apparatus of claim 10, wherein the electromagnetic signal comprises combinations of the original signal Fourier components and signal components that are generated by nonlinearities of biologic tissue as a result of application of the original signal to the biologic tissue being addressed.

12. The apparatus of claim 1, wherein the peak amplitude is between 100 and 300 V/cm.

13. A method of arresting cancerous cellular growth, comprising:
generating a current at a current generator;
modulating the current at a predetermined frequency that is greater than 10 MHz;
pulsing the current for a predetermined pulse duration that is less than about 3.0 microseconds in duration;
repeating the generation of the pulsed current at a predetermined repetition rate that is between about 1 Hz and about 20 Hz; and
providing the repeatedly-generated pulsed currents to a conductive element, wherein the conductive element comprises a coil configuration sufficient to generate an electromagnetic field when the current flows through the conductive element, wherein the electromagnetic field is adapted to induce cancer cell growth arrest and/or apoptosis in a tumor site located proximate to the conductive element without substantially affecting healthy cells in a healthy cell site also proximate to the conductive element.

14. The method of claim 13, wherein the current generator generates a bipolar sinusoidal current.

15. The method of claim 14, wherein the predetermined pulse duration is between about 1 microseconds and 2 microseconds in duration.

16. The method of claim 13, wherein the predetermined pulse duration is about 2.0 microseconds in duration.

17. The method of claim 13, wherein the predetermined frequency is greater than 10 MHz.

18. The method of claim 14, wherein the electromagnetic field comprises a peak amplitude that is greater than 100 V/cm so as to interfere with cancer cellular growth.

19. The method of claim 14, wherein the current comprises at least one of a sine, square, triangle, sawtooth, and rectangular waveform.

20. The method of claim 14, further comprising:
measuring at least one biologic or physiologic change associated with the tumor site, the at least one biologic or physiologic change including at least one of tissue impedance, specific cancer cell genotype, and specific cancer cell phenotype; and
adjusting the current based on the measured biologic or physiologic state.

21. A system for arresting cancer cell growth, comprising:
means for generating an electrical current; and
means for transforming the electrical current into an electromagnetic field adapted to induce cancer cell growth arrest and/or apoptosis in a tumor site by generating an electromagnetic field that comprises a peak amplitude greater than 100 V/cm.

22. The system of claim 21, wherein the electrical current comprises at least one of a sine, square, triangle, sawtooth and rectangular waveform.

* * * * *